(12) United States Patent
Toishi et al.

(10) Patent No.: US 8,466,435 B2
(45) Date of Patent: Jun. 18, 2013

(54) FINE PARTICLE MEASURING DEVICE

(75) Inventors: Mitsuru Toishi, Kanagawa (JP);
 Katsuhiro Seo, Kanagawa (JP); Koji Takasaki, Chiba (JP); Shinji Yamada, Kanagawa (JP); Atsushi Fukumoto, Kanagawa (JP)

(73) Assignee: Sony Corporation, Tokyo (JP)

( * ) Notice: Subject to any disclaimer, the term of this patent is extended or adjusted under 35 U.S.C. 154(b) by 167 days.

(21) Appl. No.: 13/180,740

(22) Filed: Jul. 12, 2011

(65) Prior Publication Data
 US 2012/0018650 A1 Jan. 26, 2012

(30) Foreign Application Priority Data
 Jul. 22, 2010 (JP) ................. 2010-164861

(51) Int. Cl.
 *G01N 21/64* (2006.01)
(52) U.S. Cl.
 USPC ....................................... 250/458.1
(58) Field of Classification Search
 CPC .................................... G01N 21/64
 USPC ....................................... 250/458.1
 See application file for complete search history.

(56) References Cited

U.S. PATENT DOCUMENTS
2010/0314554 A1* 12/2010 Galimberti et al. ........ 250/458.1

FOREIGN PATENT DOCUMENTS
WO 2005-103642 4/2005

* cited by examiner

*Primary Examiner* — David Porta
*Assistant Examiner* — Edwin Gunberg
(74) *Attorney, Agent, or Firm* — K&L Gates LLP

(57) ABSTRACT

A fine particle measuring device includes an optical filter that is divided into a plurality of areas and is disposed on an optical path on which light emitted from a fine particle, which is irradiated with light, is guided to an optical detector. In the fine particle measuring device, the optical filter includes a first area having wavelength selectivity by which the first area blocks reflected light from the fine particle and an unnecessary scattered light component and transmits fluorescence, and a second area that is disposed around at least the first area and has no wavelength selectivity so as to transmit a necessary scattered light component.

5 Claims, 10 Drawing Sheets

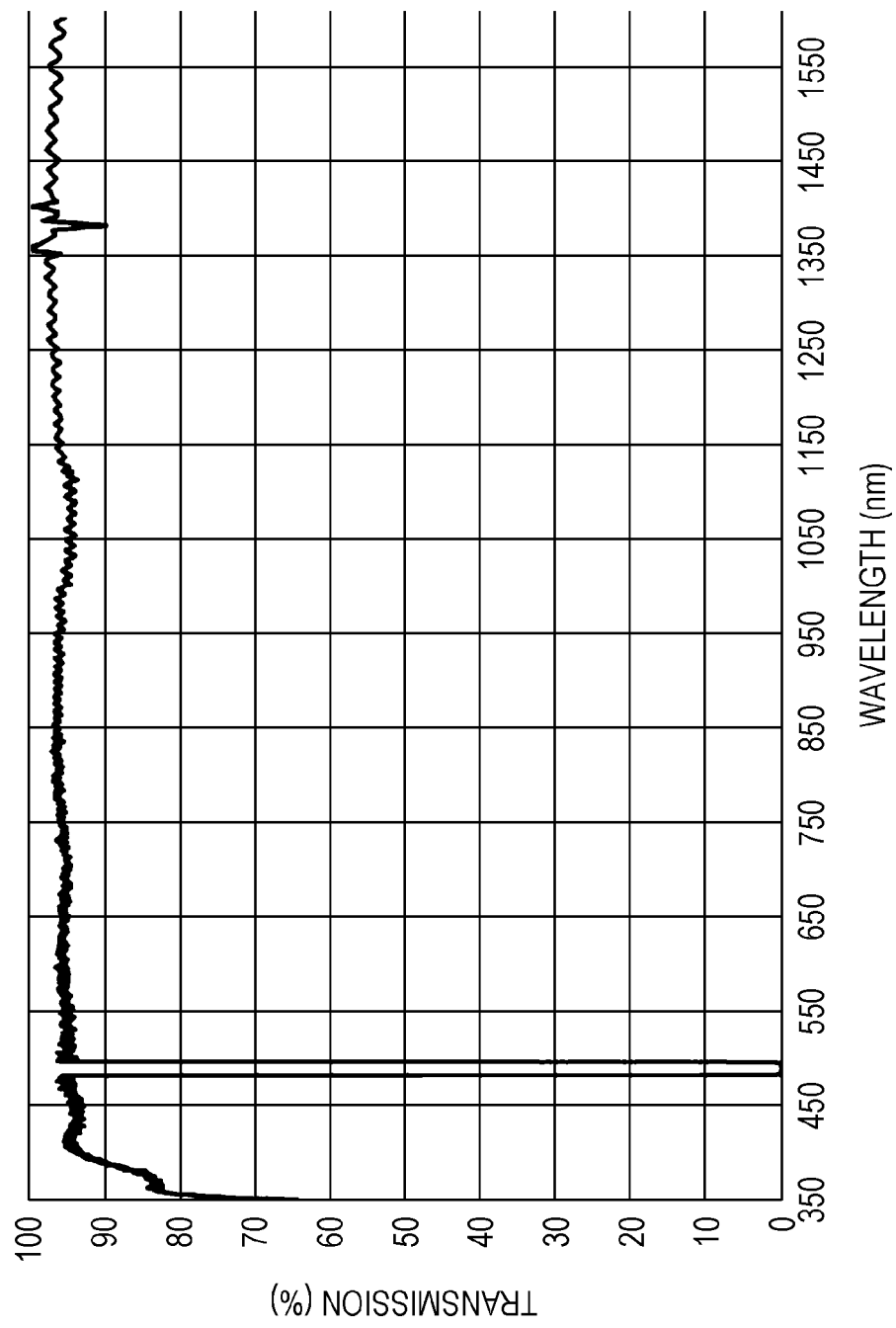

SURFACE REFLECTED LIGHT

FLUORESCENCE

FINE PARTICLE MEASURING DEVICE

CROSS REFERENCES TO RELATED APPLICATIONS

The present application claims priority to Japanese Priority Patent Application JP 2010-164861 filed in the Japan Patent Office on Jul. 22, 2010, the entire contents of which are hereby incorporated by reference.

BACKGROUND

The present application relates to a fine particle measuring device. In particular, the present application relates to a fine particle analysis device that optically analyzes a property of a fine particle.

Such fine particle measuring devices have been used that radiate light to fine particles which flow in a flow path which is formed in a flow cell or on a microchip so as to detect scattered light from the fine particles or fluorescence emitted from the fine particles or from fluorescent substances which are labeled on the fine particles and measure optical properties of the fine particles.

International Publication No. WO2005/103642 discloses a specimen discrimination device that includes a detected-light receiving optical fiber so as to measure a property with higher sensitivity. This device measures fluctuation of received light quantity of back scattered light emitted from a specimen, being able to detect a state (transmittance, absorption, or the like) of the specimen.

SUMMARY

In fine particle detection devices of the related art, in order to obtain an optimum scattering angle, it is necessary to provide a mask in an optical detection system which detects fluorescence and scattered light. The mask blocks reflected light so as to prevent a reflected light component from entering a scattered light electron multiplier or a fluorescence electron multiplier. However, a necessary light component such as fluorescence is also blocked by the mask more than necessary and therefore sensitivity of the necessary light component is degraded disadvantageously. Here, a mask which has been used in the related art is referred to below as a "common (related art) mask".

It is desirable to provide a fine particle analysis device which efficiently acquires a necessary light component, especially, back-scattered light and fluorescence.

According to an embodiment, there is provided a fine particle measuring device that includes an optical filter that is divided into a plurality of areas and is disposed on an optical path on which light emitted from a fine particle, which is irradiated with light, is guided to an optical detector. In the fine particle measuring device, the optical filter includes a first area having wavelength selectivity by which the first area blocks reflected light from the fine particle and an unnecessary scattered light component and transmits fluorescence, and a second area that is disposed around at least the first area and has no wavelength selectivity so as to transmit a necessary scattered light component.

Accordingly, the reflected light and the unnecessary scattered light component from the fine particle can be cut and the fluorescence which is one of necessary light components can be transmitted by the first area. Further, the fluorescence and the necessary scattered light component (for example, back scattered light) can be transmitted by the second area.

In the embodiment, it is preferable that the first area having the wavelength selectivity be disposed in a penetration part of the second area having no wavelength selectivity.

In the embodiment, it is preferable that a frame supporting the first area be provided on a circumference of the first area having the wavelength selectivity and the second area having no wavelength selectivity be hollow.

Accordingly, difference in refractive indexes of the first area and the second area on their interface can be reduced.

In the embodiment, it is preferable that the optical filter further include a third area having wavelength selectivity, around the second area that is disposed around the first area having the wavelength selectivity and having no wavelength selectivity. The center of a beam system can be cut by the first area and in addition, the outside of the beam system can be cut by the third area depending on necessity. Accordingly, back scattered light from a desired angle can be acquired.

In the embodiment, it is preferable that an optical fiber that guides fluorescence and back scattered light to a fluorescence and back scattered light detector be provided on the optical path and the optical filter that is divided into the plurality of areas be disposed so that light transmitted through the optical filter is received by the optical fiber. Accordingly, back scattered light and fluorescence can be detected with high sensitivity.

According to the embodiment, a fine particle analysis device that efficiently acquires back scattered light and fluorescence is provided.

Additional features and advantages are described herein, and will be apparent from the following Detailed Description and the figures.

BRIEF DESCRIPTION OF THE FIGURES

FIG. 3 illustrates a transmission spectrum of a first area of the optical filter which is provided to the fine particle analysis device according to the embodiment;

FIG. 4A illustrates a case where the first area has a circular shape, FIG. 4B illustrates a case where the first area has a square shape, FIG. 4C illustrates a case where each of first to third areas has a circular shape, and FIG. 4D illustrates a case where each of the first to third areas has a square shape;

FIG. 5A illustrates a case where a lower part of a (plane) filter of the first area is bonded on an upper part of a (plane) filter of the second area, FIG. 5B illustrates a case where the (plane) filter of the first area is disposed in a penetration part of the (plane) filter of the second area and an upper surface of the (plane) filter of the first area is protruded more than an upper surface of the (plane) filter of the second area, and FIG. 5C illustrates a case where the first area is disposed in the penetration part of the (plane) filter of the second area and the upper and lower surfaces of the first area and the second area are coplanar;

FIG. 7A illustrates flow paths of reflected light, back scattered light, and fluorescence when using the reflective optical filter, and FIG. 7B illustrates a transmission spectrum of the first area of the reflective optical filter of the modification;

DETAILED DESCRIPTION

Embodiments of the present application will be described below in detail with reference to the drawings.

Here, it should be noted that embodiments described below are major examples of embodiments and the scope is not limitedly interpreted due to these embodiments. The descriptions will be shown in the following order.

1. Configuration of Fine Particle Measuring Device
(1) Optical Detection Unit
(1-1) FL/BS Condensing System-Optical Filter
2. Operation of Fine Particle Measuring Device
3. Modification
(1) Reflective Optical Filter
(2) Operation in Case Where Reflective Optical Filter Is Provided 1. Configuration of Fine Particle Measuring Device>

Figure 1:
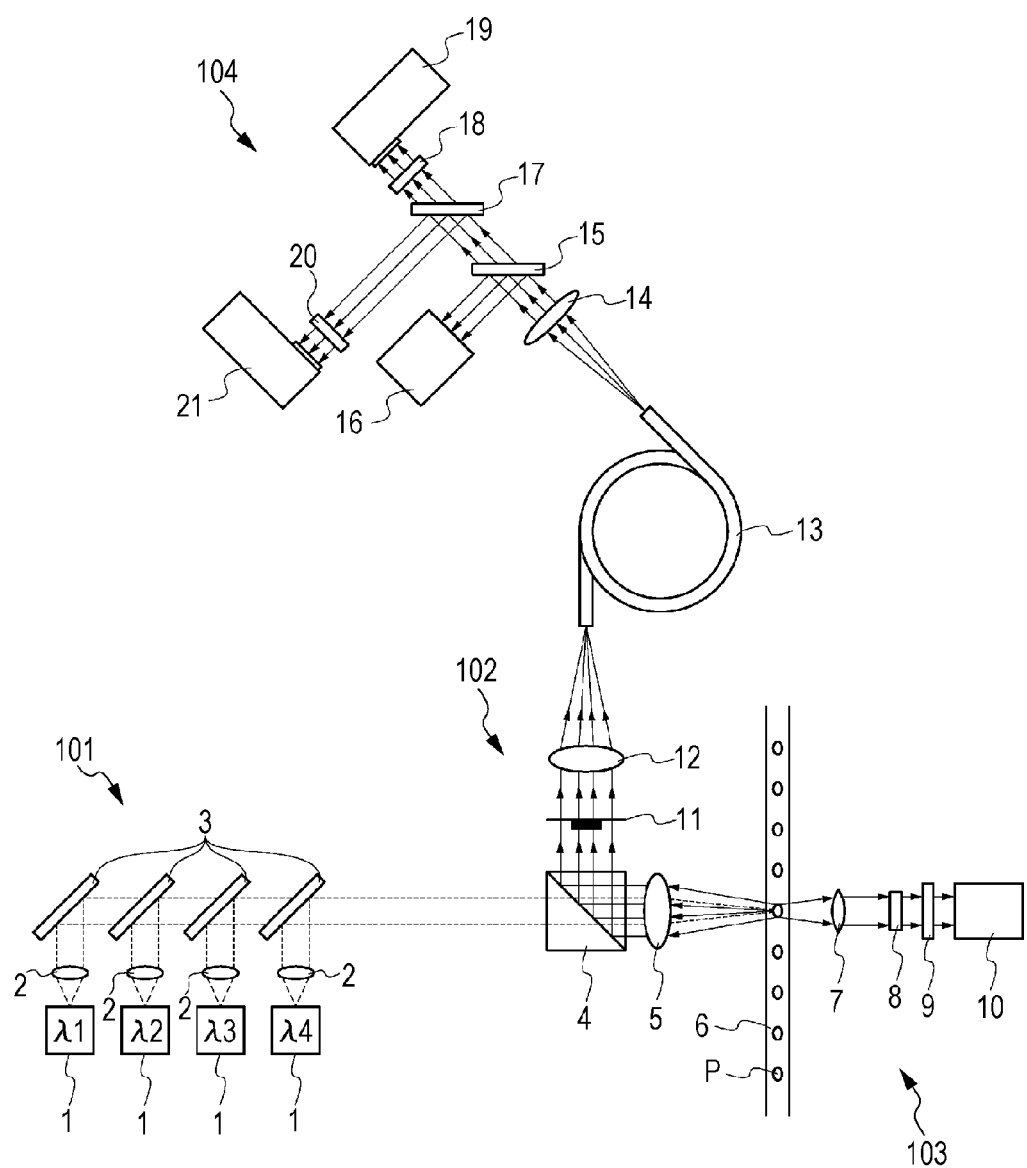
FIG. 1 illustrates an optical path of a fine particle analysis device according to an embodiment.

FIG. 1 schematically illustrates the configuration of a fine particle measuring device according to an embodiment and especially, illustrates an optical detection system (optical flow path).

The fine particle measuring device includes a flow path system such as a flow cell and a microchip, and an optical detection unit that detects a plurality of light components such as fluorescent, back scattered light, and front scattered light which are emitted from fine particles P which flow in a flow path formed in the flow cell or formed on the microchip. Here, the fine particle measuring device may include a sort unit that collects or separates measured fine particles P, as necessary.

(1) Optical Detection Unit

As shown in FIG. 1, the optical detection unit is composed of an optical irradiation system 101, a fluorescence and back scattered light condensing system 102, a front scattered light detection system 103, and a fluorescence and back scattered light detection system 104. Accordingly, light components emitted from fine particles which are irradiated with light can be introduced respective optical detectors so as to detect and measure desired light components.

The optical irradiation system 101 includes light sources ($\lambda 1$ to $\lambda 4$) 1 which radiate light (exciting light), condenser lenses 2 which respectively convert the light from the light sources 1 into parallel light, and dichroic mirrors 3 which arrange the light on the same axis.

The light (exciting light) radiated from the optical irradiation system 101 passes through a half mirror 4 and an objective lens 5 which are included in the fluorescence and back scattered light (referred to below as FL/BS, as well) condensing system so as to be radiated to fine particles P which flow in a flow path 6. At this time, not only fluorescence and necessary scattered light components but also reflected light and unnecessary scattered light components are emitted from the fine particles P.

Here, the fluorescence and the necessary scattered light components are important light components for acquiring optical information (property) of the fine particles P. The necessary scattered light components are back scattered light and side scattered light, for example. The unnecessary scattered light components are generated when the radiated light (exciting light) hits the flow path system, a substrate, a cell, or the like.

In the embodiment, "fine particles" widely include biologically-relevant fine particles such as a cell, a microorganism, and a liposome, synthetic particles such as a latex particle, a gel particle, and an industrial particle, and the like.

The biologically-relevant fine particles include a chromosome, a liposome, a mitochondrion, an organelle, and the like which constitute various cells. Intended cells include an animal cell (a hemocyte cell and the like), a plant cell, and the like. Intended microorganisms include bacteria such as coli bacteria, viruses such as tobacco mosaic viruses, fungi such as yeast, and the like. Further, the biologically-relevant fine particles also can include biologically-relevant polymer such as nucleic acid, protein, and a complex of nucleic acid and protein.

The industrial particles may be organic/inorganic polymer materials, metals, or the like, for example. The organic polymer materials include polystyrene, styrene-divinylbenzene, polymethyl methacrylate, and the like. The inorganic polymer materials include glass, silica, a magnetic body material, and the like. Metals include gold colloid, aluminum, and the like.

The shape of the fine particles mentioned above is commonly spherical, but it may be nonspherical, and the size, the mass, and the like are not specifically limited.

The front scattered light (also referred to below as FS) detection system 103 includes a FS condenser lens 7, a FS mask 8 which cuts front scattered light by a desired angular component, a bandpass filter 9 which transmits only a desired wavelength component, and a FS optical detector 10 which detects the transmitted light.

The fluorescence and back scattered light condensing system 102 includes the objective lens 5 which condenses light components from fine particles P, the half mirror 4 which reflects these light components on its surface, an optical filter 11 which is divided into a plurality of areas to which the light components are guided, and a FL/BS condenser lens 12.

Here, the optical filter (referred to below as a notch filter mask as well as the optical filter) 11 which is divided into the plurality of areas blocks (reduces) reflected light and unnecessary scattered light components from the light components which are reflected by the half mirror 4 and transmits necessary light components (for example, fluorescence and back scattered light). The FL/BS condenser lens 12 guides the necessary light components to the optical fiber 13.

The fluorescence and back scattered light detection system 104 detects fluorescence and back scattered light of the light components which are received from the optical fiber 13.

Specifically, the fluorescence and back scattered light detection system 104 includes a FL/BS condenser lens 14 which converts the light components from the optical fiber 13 into parallel light, a notch filter 15 which reflects back scattered light of the parallel light and transmits fluorescence, and a BS optical detector 16 which detects the back scattered light. The fluorescence and back scattered light detection system 104 further includes a FL dichroic mirror 17 which transmits desired wavelength components among fluorescence components which pass through the notch filter 15 and reflects other wavelength components, FL bandpass filters 18 and 20 which further select the desired wavelength components, and optical electron multipliers 19 and 21 which detect the desired wavelength components.

Here, the numbers of notch filter masks, dichroic mirrors, bandpass filters, optical electron multipliers, and optical detectors may be increased or decreased depending on necessity.

The optical irradiation system 101, the front scattered light detection system 103, and the fluorescence and back scattered light detection system 104 of the fine particle measuring device described above may have the configurations same as those of a fine particle measuring device of the related art.

(1-1) FL/BS Condensing System-Optical Filter

The FL/BS condensing system 102 and the optical filter 11 which is provided to the FL/BS condensing system 102 in the fine particle measuring device according to the embodiment are described below in reference to FIGS. 2A to 6. The optical filter 11 is first described.

The optical filter 11 is used to reduce reflected light from the light components from the fine particles P and unnecessary scattered light components and obtain fluorescence components and necessary scattered light components (especially, back scattered light components) with high efficiency. Therefore, on an approximate central part of the optical filter 11, a filter of a first area 111 on which (surface) reflected light from the fine particles P and unnecessary scattered light components are incident is disposed (refer to FIGS. 2A and 2B, for example). The filter of the first area 111 has specific-wavelength selectivity. Thanks to this specific-wavelength selectivity, reflected light and unnecessary scattered light components can be blocked (reduced) and fluorescence components can be transmitted.

It is sufficient for the filter of the first area 111 to have a transmission spectrum such that the filter can reflect only desired unnecessary light components with high accuracy and can transmit necessary light components. More specifically, since wavelengths of incident light and reflected light are commonly smaller than a fluorescence wavelength, a filter which does not transmit a low wavelength component is favorably used.

For example, as shown in FIG. 3, as the filter, which has specific-wavelength selectivity, of the first area 111, a filter which does not transmit only a specific-wavelength component having a wavelength of approximately 488 nm, specifically, 480 nm to 500 nm is favorably used. It is favorable to prepare such filter that has a property in which only transmittance with respect to a specific-wavelength component is five digits lower than transmittance with respect to other components, as the filter having the wavelength selectivity. Accordingly, the filter can block (reduce) reflected light and unnecessary scattered light components and transmit fluorescence components with high accuracy, thereby being able to acquire higher quantity of fluorescence with high efficiency.

Figure 10A:
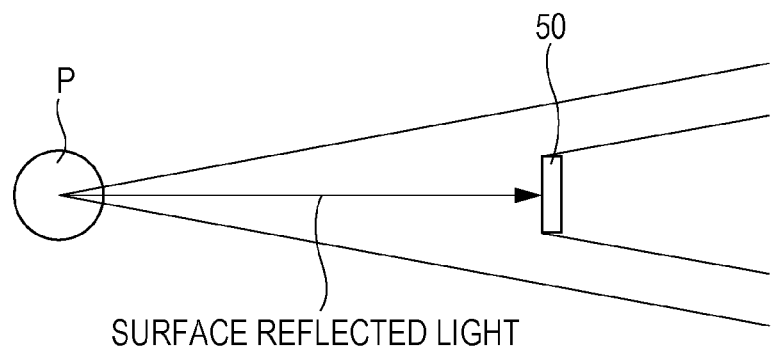
FIGS. 10A and 10B illustrate reflected light, back scattered light, and fluorescence which are emitted from fine particles irradiated with a laser beam in the fine particle analysis device provided with a common (related art) mask.
Figure 10B:
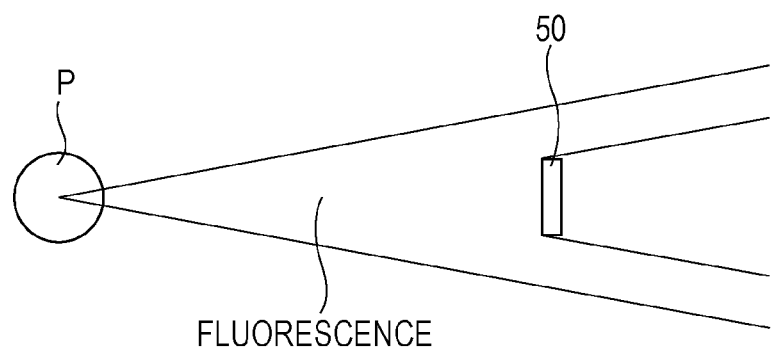

FIGS. 10A and 10B illustrate reflected light, back scattered light, and fluorescence which are emitted from the fine particles P when a mask of the related art is used. Thus, fluorescence as well as surface reflected light is blocked by the common mask. Accordingly, the light quantity of fluorescence incident on the optical detector is reduced and fluorescence sensitivity is deteriorated.

Figure 2A:
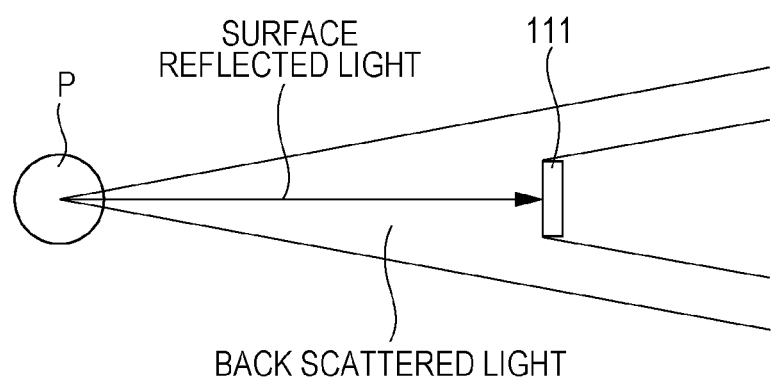
FIGS. 2A and 2B illustrate reflected light, back scattered light, and fluorescence which are emitted from fine particles irradiated with a laser beam in the fine particle analysis device having an optical filter according to the embodiment.
Figure 2B:
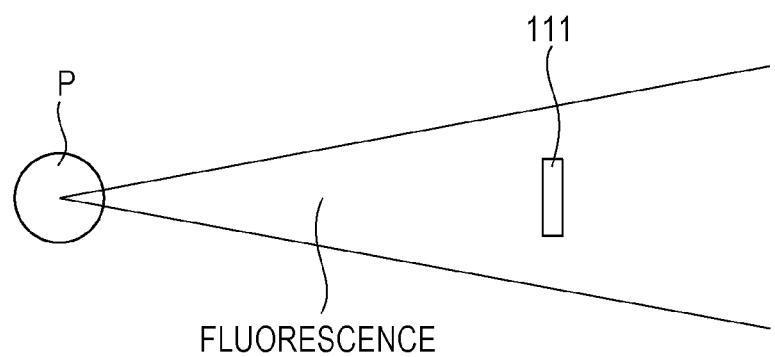

In contrast, as shown in FIG. 2A, the filter of the first area 111 has the specific-wavelength selectivity as described above, so that the filter transmits fluorescence while blocking reflected light, of which a propagation angle is small, from the fine particles P and unnecessary scattered light components. Further, as shown in FIG. 2B, propagation angles of back scattered light and fluorescence are larger than propagation angles of reflected light components in principle, so that necessary light components (back scattered light components and fluorescence components) pass through the periphery of the filter of the first area 111. Accordingly, loss in the light quantity of fluorescence incident on the optical detector can be reduced. Further, back scattered light also can be acquired, so that the back scattered light and the fluorescence can be simultaneously acquired with high efficiency. In addition, it is enough to mount the optical filter on the fine particle measuring device, and thus the fine particle measuring device does not have to have the complicated configuration. Accordingly, an optical detector and a fine particle measuring device that can acquire back scattered light and fluorescence with high efficiency can be simply and compactly realized.

FIGS. 4A to 5C show examples of the optical filter 11 which includes the first area having the specific-wavelength selectivity described above and a second area which is disposed around at least the first area and has no wavelength selectivity. However, the shape and the configuration of the optical filter 11 are not limited to these examples.

Figure 4A:
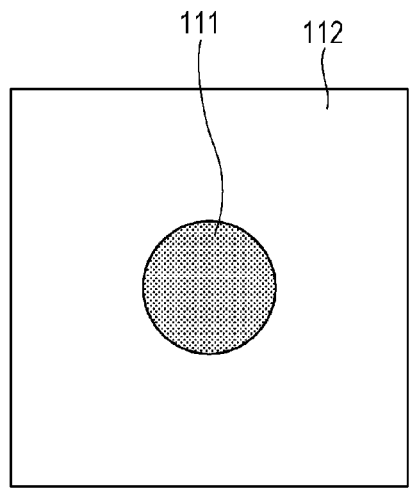
FIGS. 4A to 4D show examples of the optical filter (upper surface direction) provided to the fine particle analysis device according to the embodiment.
Figure 4B:
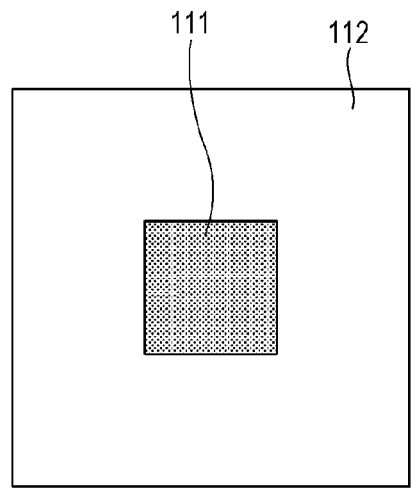

First, the optical filter 11 including the filter of the first area 111 having the specific-wavelength selectivity and a filter of a second area 112 disposed around the first area 111 and having no wavelength selectivity as shown in FIGS. 4A and 4B is described.

The optical filter 11 includes the filter of the first area 111 and the filter of the second area 112. The filter of the first area 111 is disposed on the approximate center of the optical filter. The approximate center is a part on which light components such as reflected light and unnecessary scattered light components are incident.

The filter of the first area 111 has specific-wavelength selectivity by which the filter blocks reflected light from the fine particles P and unnecessary scattered light components and transmits fluorescence.

The filter of the second area 112 has no specific-wavelength selectivity and transmits fluorescence and necessary scattered light components. Here, as the filter having no specific-wavelength selectivity, not a filter (optical material) used in the first area 111 described above but a filter (for example, glass or the like) which transmits back scattered light and fluorescence may be used.

Figure 5A:
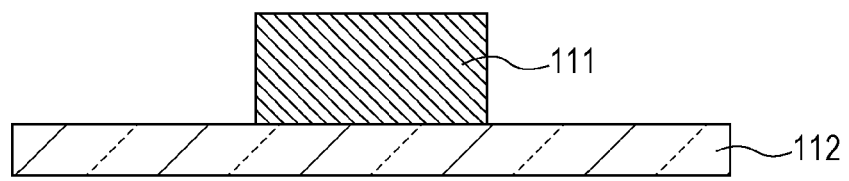
FIGS. 5A to 5C show examples of a section in the horizontal direction of the optical filter provided to the fine particle analysis device according to the embodiment.
Figure 5B:
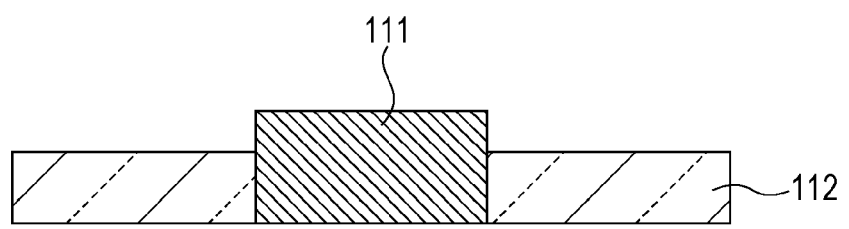
Figure 5C:
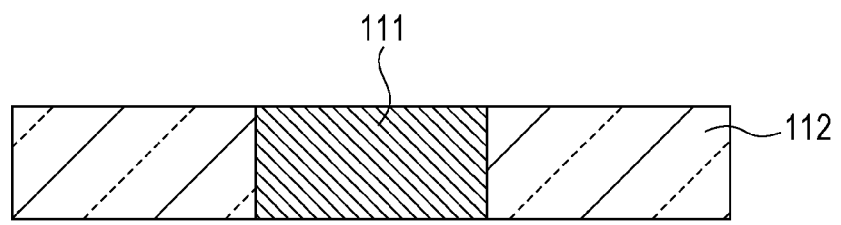

FIGS. 5A to 5C show examples of a section in the horizontal direction of the optical filter of FIG. 4A. However, the configuration of the optical filter is not limited to these examples.

In the optical filter 11 shown in FIG. 5A, the filter of the first area 111 is bonded on the approximate center of an upper surface of the filter of the second area 112. In the bonding of the filters, an adhesive or light curing resin which does not inhibit optical properties of the filters of the first area 111 and the second area 112 is favorably used. Further, it is favorable to apply anti reflection (AR) coating on a surface of the filter of the second area 112 in the bonding-type optical filter shown in FIG. 5A so as to prevent reflection in a visible range.

In the optical filter 11 shown in FIGS. 5B and 5C, a through hole or a non-through hole is formed on the approximate center of the filter of the second area 112 and the filter of the first area 111 is fit or inserted to be disposed in the through hole or the non-through hole. Further, the filter of the first area 111 may be protruded from an upper surface and/or a lower surface of the filter of the second area 112 as shown in FIG. 5B. Furthermore, the filter of the first area 111 may be formed to be coplanar with the upper surface and/or the lower surface of the filter of the second area 112 as shown in FIG. 5C. Here, the filter of the first area 111 and the filter of the second area 112 may be layered in the horizontal direction or the height direction.

By forming the optical filter in which one area is disposed in a through hole of the other area as shown in FIGS. 5B and 5C, performance degradation of the filter, which easily occurs due to different refractive indexes on an interface in the case of the optical filter shown in FIG. 5A, can be reduced.

Figure 4C:
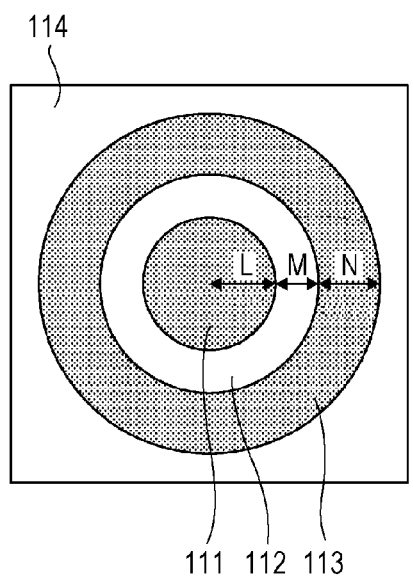
Figure 4D:
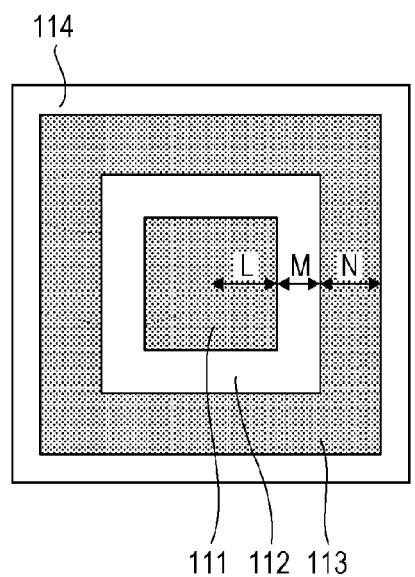

The optical filter 11 shown in FIGS. 4C and 4D further includes a third area having wavelength selectivity around the second area which is disposed around the first area having the specific-wavelength selectivity and has no specific-wavelength selectivity.

In the optical filter 11 shown in FIGS. 4C and 4D, a filter of a third area 113 having a specific-wavelength property is further disposed around the filter of the second area 112 which is disposed around the filter of the first area 111. Back scattered light commonly has angular dependency with respect to a particle size, and there is a case necessary to acquire only scattered light having desired angular components. In this case, by employing the configuration of the optical filter 11 shown in FIGS. 4C and 4D, the center of the beam system can be cut by the filter of the first area 111 and further, the outside of the beam system can be also cut by the filter of the third area 113. Accordingly, back scattered light from a desired angle can be acquired.

At this time, it is favorable to set the width L of the first area 111, the width M of the second area 112, and the width N of the third area 113 to be respectively 0 mm to 4 mm, 4 mm to 6 mm, and 6 mm to 8 mm from the center so as to acquire desired back scattered light.

Here, the width L is a distance of a radius of the first area 111. The width M is obtained by a distance from the center of the first area 111 to a circumference of the second area 112— the width L. The width N is obtained by a distance from the center of the first area 111 to a circumference of the third area 113−(the width L+the width M). In a case of a polygon, the width depends on a distance from the center to an outer side (the length of a perpendicular).

The optical filter 11 shown in FIGS. 4C and 4D can be formed by bonding or fitting the filters of respective areas as described above.

It is sufficient to prepare the optical filter described above by combining at least two kinds of optical materials (filters) having different wavelength properties from each other such as an optical material having a specific-wavelength property and an optical material having no wavelength property.

A method for forming an optical filter in which two or more kinds of optical materials having different optical properties from each other are used is not specifically limited, so that a method for forming photonic crystal, for example, an etching method (for example, semiconductor lithography method) may be used as well as the method described above. The method for forming photonic crystal is favorable because it is easy to form the optical filter 11 in which respective areas are layered, as well.

Figure 6:
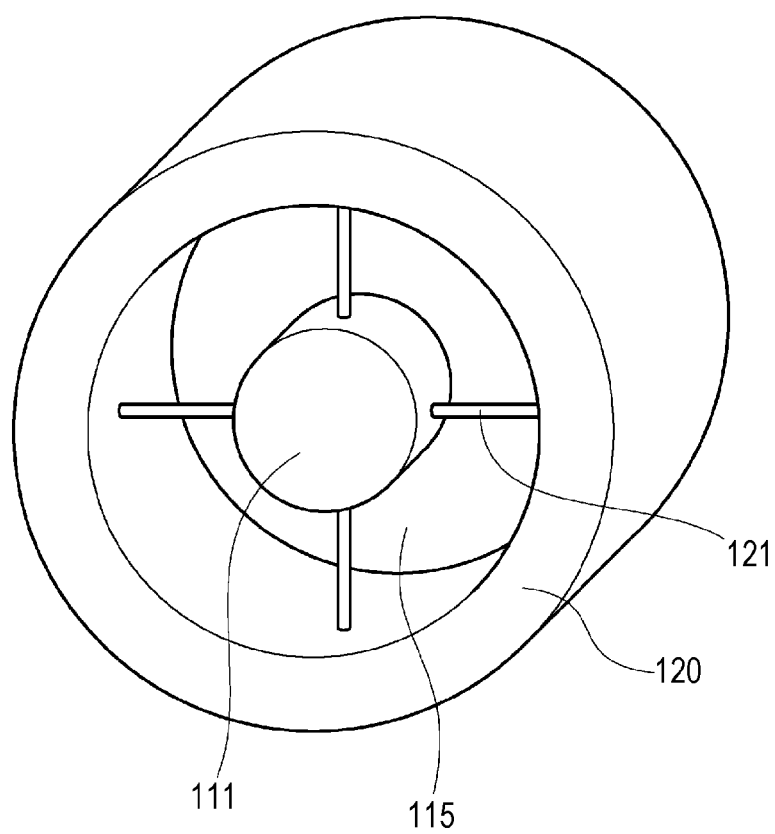
FIG. 6 illustrates an optical filter which is provided to the fine particle analysis device according to the embodiment and shows a case where the (plane) filter of the first area is supported by a cylindrical frame and the second area is hollow.

Further, the optical filter 11 which includes the filter of the first area 111 and a cylindrical frame 120 which supports the filter of the first area 111 via a single or a plurality of wires 121 as shown in FIG. 6 may be used. Further, it is favorable that the filter of the first area 111 is disposed on the approximate center of the frame 120 and a space 115 which is positioned around the first area and is hollow is used as the second area. By employing such simple configuration, performance degradation which easily occurs due to difference of filter materials can be reduced.

The optical filter 11 is provided to the FL/BS condensing system as described above. It is favorable that the optical filter 11 is disposed in front of the optical fiber 13 which guides fluorescence and back scattered light to the FL/BS optical detection system (the fluorescence and back scattered light detector). Specifically, it is favorable to dispose the optical filter such that the optical fiber can receive light transmitted through the optical filter.

By employing such configuration, loss in the light quantity of fluorescence can by reduced more than a case where the optical filter 11 is disposed in the FL/BS optical detection system.

2. Operation of Fine Particle Measuring Device

An operation of the fine particle measuring device provided with the optical filter described above is described below with reference to FIG. 1.

Light beams (exciting light) from respective laser light sources 1 of a plurality of different wavelengths in the optical irradiation system 101 are converted into parallel light by corresponding condenser lenses 2 so as to be disposed on the same axis by the dichroic mirrors 3. The light beams (exciting light) pass through the half mirror 4 and the objective lens 5 of the FL/BS condensing system 102 so as to be radiated to fine particles P in the flow path 6. Then, fluorescence, necessary scattered light components (front scattered light, back scattered light, and the like), and reflected light are emitted from the fine particles P and unnecessary scattered light components and reflected light are also generated.

The front scattered light of the fine particles P at this time is guided through the FS condenser lens 7, the FS mask 8, and FS bandpass filter 9 to the FS optical detector 10 in the FS detection system 103.

The reflected light, fluorescence, and the necessary scattered light components (back scattered light and the like) which are from the fine particles P, and the unnecessary scattered light components pass through the condenser lens 5 of the FL/BS condensing system 102 and are reflected by the half mirror 4 so as to pass through the notch filter mask (the optical mask) 11. At this time, the reflected light, the unnecessary scattered light components, and the front scattered light which are on the center of the light components are blocked and the fluorescence components are transmitted by the filter of the first area 111 which is positioned on the approximate center of the notch filter mask 11. Further, since the back scattered light and the fluorescence have wider propagation angles than the reflected light components, the back scattered light and the fluorescence pass through the filter of the second area 112 which is disposed around the filter of the first area 111. Thus, the back scattered light and the fluorescence transmitted through the notch filter mask 11 travel through the FL/BS condenser lens 12 so as to be coupled to the optical fiber 13.

The back scattered light and the fluorescence coming out of the optical fiber 13 are converted into parallel light by the FL/BS condenser lens 14, and the back scattered light is guided to the BS optical detector 16 by the notch filter 15 which reflects only the back scattered light so as to be detected by the BS optical detector 16. Further, the fluorescence travels through the notch filter 15, the FL dichroic mirror 17, and then the FL bandpass filter 18, thus desired wavelength components are selected among the fluorescence components, and the selected components are detected by the optical electron multiplier 19. In addition, the fluorescence travels through the notch filter 15, the FL dichroic mirror 17, and then the FL bandpass filter 20, thus desirable wavelength components of the fluorescence components are further selected, and the selected components are detected by the optical electron multiplier 21 in the same manner.

3. Modification (1) Reflective Optical Filter

Figure 7A:
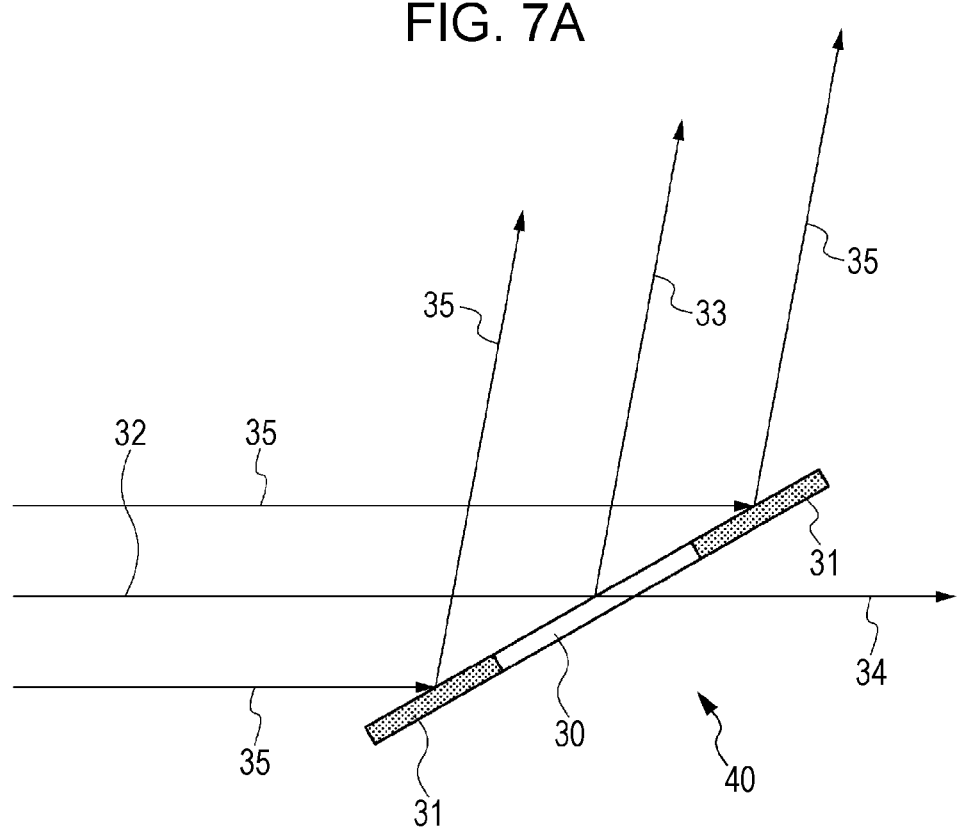
FIGS. 7A and 7B show an example of an optical filter (reflective optical filter) according to a modification.

The optical filter 11 provided to the FL/BS condensing system 102 may be exchanged for a reflective optical filter 40 shown in FIG. 7A.

The reflective optical filter 40 includes a first area 30 having specific-wavelength selectivity and a second area 31 disposed around the first area 30 and having no wavelength selectivity. The first area 30 has wavelength selectivity by which the first area 30 transmits reflected light from the fine particles P and unnecessary scattered light components and reflects fluorescence. The second area 31 has no wavelength selectivity and reflects necessary light components (for example, fluorescence from the fine particles P and necessary scattered light components such as back scattered light components).

More specifically described, the reflective optical filter 40 includes a bandpass filter 30 on the approximate center thereof and a mirror 31 on both ends of the bandpass filter 30. The bandpass filter 30 transmits reflected light from the fine particles P and unnecessary scattered light components and reflects fluorescence.

Figure 7B:
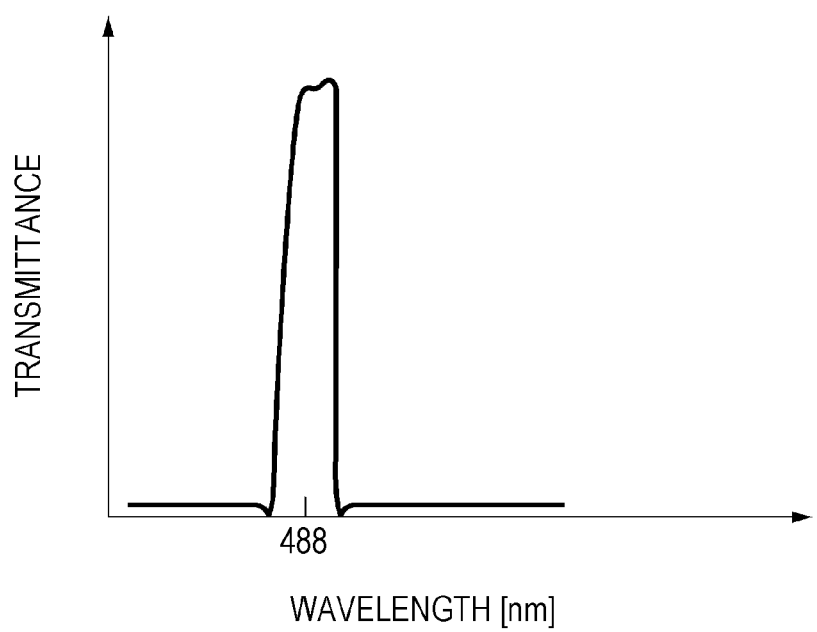

FIG. 7B shows an example of a transmission spectrum of the bandpass filter 30.

The filter of the first area of the reflective optical filter has a spectrum such that the filter of the first area can transmit only desired unnecessary light components with high accuracy and reflects necessary light components in an opposite manner to the property of the filter of the first area 111 of the optical filter described above. Specifically, the bandpass filter 30 (the filter of the first area) has wavelength selectivity which is opposite to the transmission spectrum of the filter of the first area 111 of the optical filter 11, and for example, the bandpass filter 30 transmits light components of the wavelength of about 488 nm, specifically, from 480 nm to 500 nm and reflects light components of other wavelength.

On the other hand, the mirror 31 reflects light components in the whole wavelength range, that is, has no wavelength selectivity.

By employing the reflective optical filter 40, a light utilization ratio becomes higher than that of the optical filter 11 because reflected components are used as fluorescence components and the like.

It is sufficient that the FL/BS condensing system 102 provided with the reflective optical filter 40 is configured such that light components (for example, back scattered light and fluorescence components) reflected by the reflective optical filter 40 are received by the optical fiber 13. For example, a mirror which reflects back scattered light and fluorescence may be provided in front of the condenser lens 12 in the FL/BS condensing system 102 or a position of a light receiving part of the optical fiber 13 may be changed.

(2) Operation in Case Where Reflective Optical Filter Is Provided

As shown in FIG. 7A, light components (reflected light, back scattered light, and fluorescence) from the fine particles P and unnecessary scattered light components are guided to the reflective optical filter 40. Since a propagation angle of the reflected light is small among these components, the reflected light passes through the bandpass filter 30 (first area) which is positioned on the approximate center of the reflective optical filter 40. Since a propagation angle of the back scattered light is large, the back scattered light is radiated on the whole surface of the mirror of the reflective optical filter 40. At this time, the back scattered light passes through the bandpass filter 30 (first area) which is positioned on the approximate center and are reflected by the mirror 31 (second area) provided around the bandpass filter 30. Since a propagation angle of the fluorescence is large, the fluorescence is radiated on the whole surface of the mirror of the reflective optical filter 40. At this time, the fluorescence is reflected by the bandpass filter 30 (first area) which is positioned on the approximate center and by the mirror 31 (second area) provided around the bandpass filter 30.

The fluorescence and the back scattered light which are reflected are guided through a reflection mirror (not shown) to the optical fiber 13.

The shape and the configuration of the reflective optical filter 40 are not specifically limited as long as necessary light components (for example, fluorescence and necessary scattered light components such as back scattered light components) can be reflected. However, the same shape and configuration as those of the optical filter 11 are favorable. For example, the shapes and the configurations shown in FIGS. 4A to 5C are favorable. At this time, surfaces, on which light components from the fine particles P and unnecessary scattered light components are radiated, of the reflective optical filter 40 are formed to be coplanar so as to efficiently reflect fluorescence and back scattered light.

EXAMPLES

Advantageous Effects when the Optical Filter 11 is Used are Described Below

Manufacturing Example 1

Optical Filter Provided to the Fine Particle Measuring Device According to the Embodiment The filter of the first area having the wavelength property had the spectrum shown in FIG. 3. The filter of the first area had a property in which transmittance only with respect to components of desired wavelength which was 488 nm was five digits lower than the transmittance with respect to other transmission components.

As the filter of the second area having no wavelength property, a commercial cover glass was used and the AR coating for preventing reflection in a visible range was applied to the cover glass.

The filter of the first area was cut so as to have a radius of 4 mm to 5 mm and bonded on the filter of the second area, thus manufacturing a notch filter mask having the shape and the configuration shown in FIGS. 4A and 5A.

Test Example 1

Measurement of Fluorescence Sensitivity by Respective Fine Particle Measuring Devices In the following experiment, eight kinds of beads having different brightness from each other were used and fluorescence was obtained by irradiating the beads with exciting light having the wavelength of 488 nm. Peaks of histograms when using a common mask shown in FIG. 8A, when using a notch filter mask shown in FIG. 8B, and when using no mask shown in FIG. 8C were compared.

Here, in this experiment, a state that all of the peaks of the histograms of the eight beads independently exist is a state with high sensitivity. A peak having the lowest intensity (leftmost peak) is a peak of a bead on which a fluorescence substance is not attached, so that this component is a noise component. Accordingly, a state that the noise component and other peaks are completely separated is a state with high sensitivity, being favorable.

Figure 8A:
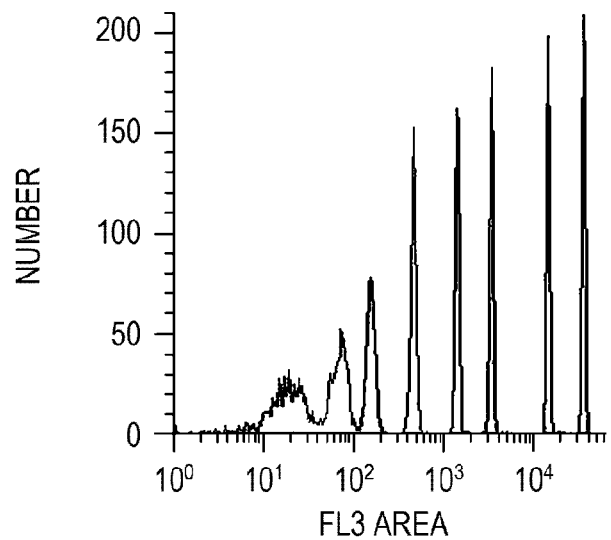
FIG. 8A illustrates a measurement result of fluorescence sensitivity obtained with a fine particle analysis device provided with a common (related art) mask.
Figure 8B:
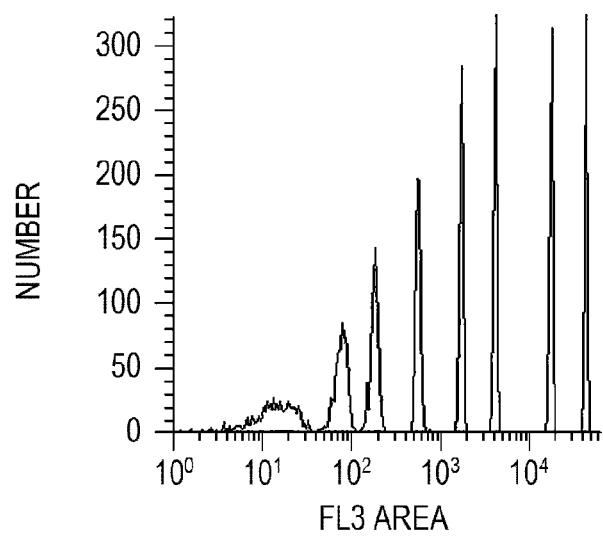
FIG. 8B illustrates a measurement result of fluorescence sensitivity obtained with a fine particle analysis device provided with a mask having areas of different transmission wavelengths according to the embodiment.
Figure 8C:
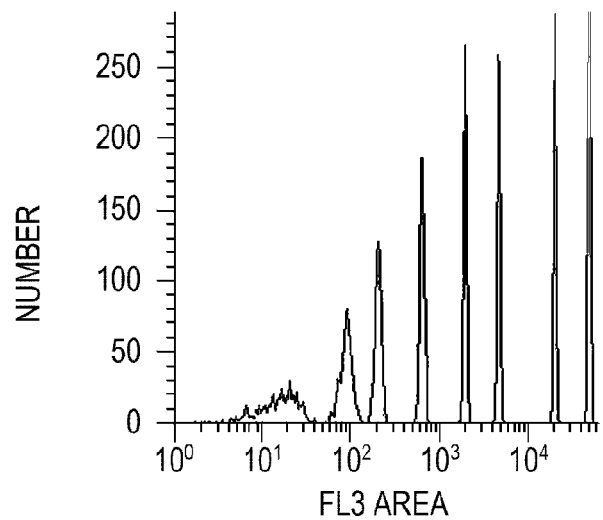
FIG. 8C illustrates a measurement result of fluorescence sensitivity obtained with a fine particle analysis device provided with no mask.

In the experiments of FIGS. 8A and 8B, masks having the same size of which a side is 4.5 mm were used.

When the common mask was used in the experiment of FIG. 8A, the sixth, seventh, and eighth peaks from the right were connected with each other but when the notch filter mask was used in the experiment of FIG. 8B, the seventh and eighth peaks were separated from each other. This had a nearly same property as that when using no mask in the experiment of FIG. 8C. Therefore, it could be confirmed that there was no loss in the light quantity of fluorescence when the notch filter mask was used.

Test Example 2

Measurement of Scattering Light by Respective Fine Particle Measuring Devices

A blood sample divided into three kinds of cells was used. Signals of front scattered light and back scattered light vary depending on the sizes of the cells and complexity of the cells. Of course, when the sizes of the masks of the back scattered light were not optimized or an extinction ratio of the masks was poor, the property was deteriorated.

Figure 9A:
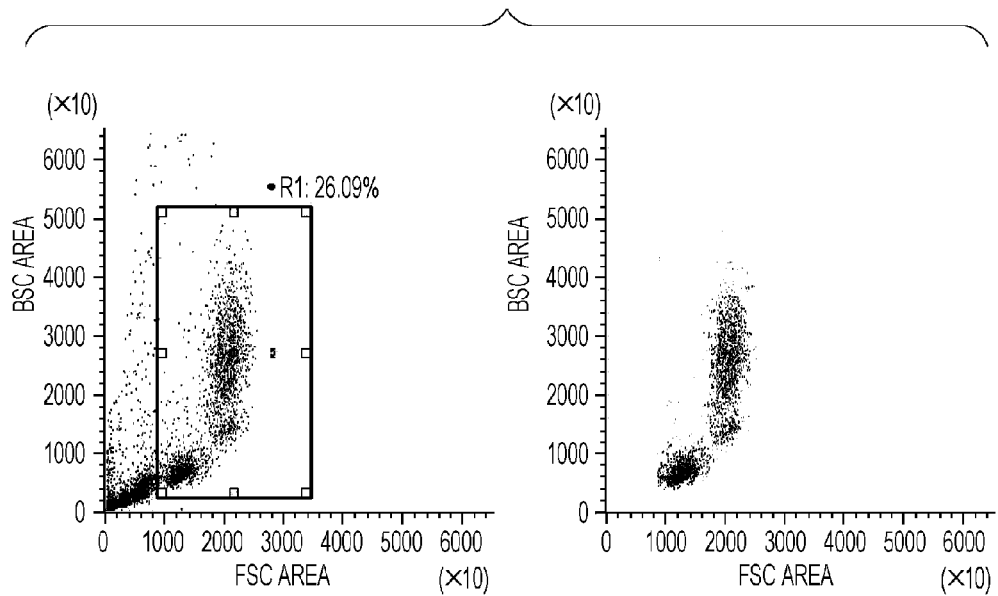
FIG. 9A illustrates a measurement result of back scattered light obtained with a fine particle analysis device provided with a common (related art) mask.
Figure 9B:
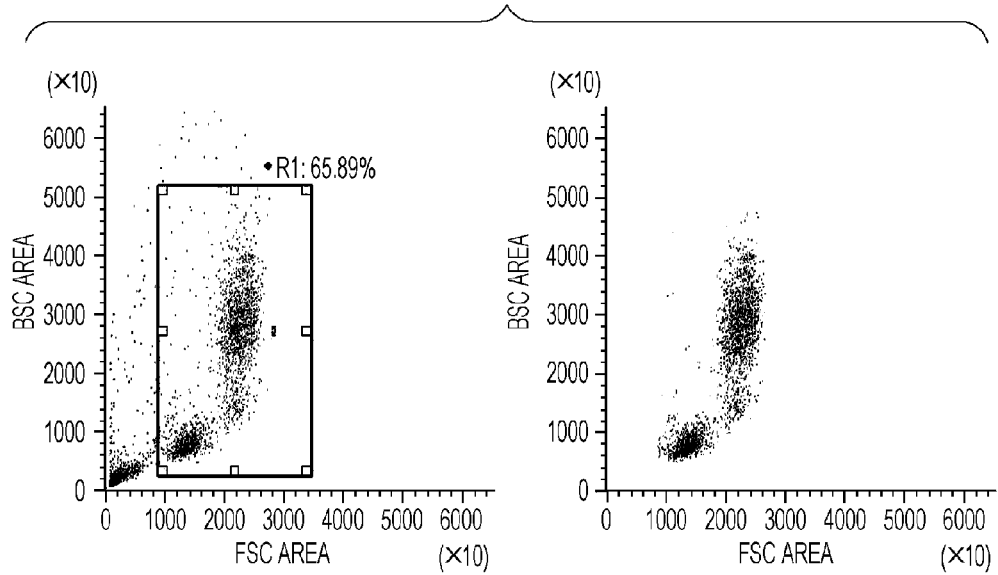
FIG. 9B illustrates a measurement result of back scattered light obtained with a fine particle analysis device provided with a mask having areas of different transmission wavelengths according to the embodiment.

In the experiments using respective masks shown in FIGS. 9A and 9B described above, masks having the same size of which a side was 4.5 mm were used.

Nearly the same result as a result which was obtained when central light was completely blocked with the common mask and shown in FIG. 9A was obtained when the notch filter mask was used as shown in FIG. 9B.

From the above described two tests, it was confirmed that the optical filter (area divided filter) used in the device according to the embodiment functioned as a filter with respect to predetermined wavelengths and blocks them without any loss in the light quantity of fluorescence and the like.

It should be understood that various changes and modifications to the presently preferred embodiments described herein will be apparent to those skilled in the art. Such changes and modifications can be made without departing from the spirit and scope and without diminishing its intended advantages. It is therefore intended that such changes and modifications be covered by the appended claims.

The invention claimed is:

1. A fine particle measuring device, comprising:
an optical filter that is divided into a plurality of areas and is disposed on an optical path on which light emitted from a fine particle, the fine particle being irradiated with light, is guided to an optical detector; wherein
the optical filter includes
a first area having wavelength selectivity by which the first area blocks reflected light from the fine particle and an unnecessary scattered light component and transmits fluorescence, and
a second area that is disposed around at least the first area and has no wavelength selectivity so as to transmit a necessary scattered light component.

2. The fine particle measuring device according to claim 1, wherein the first area having the wavelength selectivity is disposed in a penetration part of the second area having no wavelength selectivity.

3. The fine particle measuring device according to claim 1, wherein a frame supporting the first area is provided on a circumference of the first area having the wavelength selectivity and the second area having no wavelength selectivity is hollow.

4. The fine particle measuring device according to claim 1, wherein the optical filter further includes a third area having wavelength selectivity and disposed around the second area, the second area being disposed around the first area having the wavelength selectivity and having no wavelength selectivity.

5. The fine particle measuring device according to claim 1, further comprising:
an optical fiber that guides fluorescence and back scattered light to a fluorescence and back scattered light detector and is disposed on the optical path; wherein
the optical filter that is divided into the plurality of areas is disposed so that light transmitted through the optical filter is received by the optical fiber.

* * * * *